United States Patent
Georgiev et al.

(10) Patent No.: US 9,168,006 B2
(45) Date of Patent: Oct. 27, 2015

(54) SYSTEMS AND METHODS FOR WIRELESSLY CONTROLLING MEDICAL DEVICES

(75) Inventors: Emil Markov Georgiev, Hartland, WI (US); Scott William Robinson, Bayside, WI (US); Bayne Robin Upton, Hillsburgh (CA)

(73) Assignee: General Electric Company, Schenectady, NY (US)

( * ) Notice: Subject to any disclaimer, the term of this patent is extended or adjusted under 35 U.S.C. 154(b) by 660 days.

(21) Appl. No.: 13/344,488

(22) Filed: Jan. 5, 2012

(65) Prior Publication Data

US 2013/0176230 A1 Jul. 11, 2013

(51) Int. Cl.
*G06F 3/041* (2006.01)
*A61B 5/00* (2006.01)
*G06F 3/0484* (2013.01)
*G08C 17/02* (2006.01)

(52) U.S. Cl.
CPC ............ *A61B 5/7475* (2013.01); *A61B 5/0024* (2013.01); *G06F 3/0484* (2013.01); *G08C 17/02* (2013.01); *A61B 2560/0271* (2013.01); *A61B 2560/045* (2013.01)

(58) Field of Classification Search
None
See application file for complete search history.

(56) References Cited

U.S. PATENT DOCUMENTS

| | | | |
|---|---|---|---|
| 6,419,630 B1 | 7/2002 | Taylor, Jr. et al. | |
| 6,477,424 B1 | 11/2002 | Thompson et al. | |
| 7,366,934 B1 * | 4/2008 | Narayan et al. | 713/375 |
| 7,669,598 B2 | 3/2010 | Rick et al. | |
| 7,883,458 B2 | 2/2011 | Hamel | |
| 8,624,741 B2 * | 1/2014 | Batchelder et al. | 340/573.1 |
| 8,709,009 B2 * | 4/2014 | Hamel | 606/41 |
| 2005/0204310 A1 * | 9/2005 | De Zwart et al. | 715/821 |
| 2007/0271122 A1 | 11/2007 | Zaleski | |
| 2011/0001605 A1 * | 1/2011 | Kiani et al. | 340/5.6 |
| 2012/0029303 A1 | 2/2012 | Shaya | |
| 2012/0163663 A1 * | 6/2012 | Masoud et al. | 382/103 |
| 2012/0179012 A1 | 7/2012 | Saffarian | |
| 2012/0330178 A1 * | 12/2012 | Kraft et al. | 600/544 |
| 2013/0132855 A1 * | 5/2013 | Manicka et al. | 715/740 |

FOREIGN PATENT DOCUMENTS

GB 2409951 A 7/2005
WO 2006/108304 A1 10/2006

OTHER PUBLICATIONS

GB Search Report and Written Opinion from GB Application No. 1223239.3 dated Jun. 26, 2013.
Bell, Donald, "Your next universal remote could be an iPad", dated Mar. 2, 2010, CNET website: http://news.cnet.com/8301-17938_105-10462439-1.html.

* cited by examiner

*Primary Examiner* — Jason Olson
(74) *Attorney, Agent, or Firm* — Dean D. Small; The Small Patent Law Group LLC

(57) ABSTRACT

Systems and methods for wirelessly controlling medical devices are provided. One system includes a portable user interface having a housing and a communication module within the housing configured to wirelessly communicate with at least one medical device. The portable user interface also includes a display displaying a graphical user interface to control the at least one medical device remotely, wherein the displayed graphical user interface corresponds to a control interface of the at least one medical device.

22 Claims, 5 Drawing Sheets

SYSTEMS AND METHODS FOR WIRELESSLY CONTROLLING MEDICAL DEVICES

BACKGROUND OF THE INVENTION

In patient care settings, such as in a hospital, individuals must physically observe the patient periodically, which may include adjusting monitoring or other equipment connected to the patient. For example, a nurse may have to periodically enter the Intensive Care Unit (ICU) of a hospital to take readings and make device adjustments, which require the nurse to physically touch the device(s) in the ICU.

Hospital borne infections (or pathogens) may be transferred by touch, such as the point of contact with the device(s) in the ICU. The patients in the ICU are among the most vulnerable patient types due to the serious nature of their condition. Accordingly, these touches can lead to the transfer of infections, which may result in complications for the patient or even death. In particular, Healthcare-Associated Illnesses (HAIs), namely illnesses picked up while receiving care for some other condition, result in many deaths each year. This adds significant costs to healthcare.

In order to reduce HAIs, such as in the ICU, systems for cleaning or providing improved personal hygiene are conventionally used. For example, in some ICUs, a decontamination area is used for individuals entering and leaving the ICU. However, these approaches are often not effective.

SUMMARY OF THE INVENTION

In one embodiment, a portable user interface for controlling medical devices is provided. The portable user interface includes a housing and a communication module within the housing configured to wirelessly communicate with at least one medical device. The portable user interface also includes a display displaying a graphical user interface to control the at least one medical device remotely, wherein the displayed graphical user interface corresponds to a control interface of the at least one medical device.

In another embodiment, a wireless control arrangement is provided that includes at least one medical device having a communication module and a portable user interface. The portable user interface having a housing, a communication module within the housing configured to wirelessly communicate with the at least one medical device, and a display displaying a graphical user interface to control the at least one medical device remotely, wherein the displayed graphical user interface corresponds to a control interface of the at least one medical device, and the at least one medial device and the portable user interface communicate via the communication modules.

In yet another embodiment, a method for controlling a medical device is provided. The method includes detecting one or more wirelessly controllable medical devices, receiving a user input at a portable electronic device to remotely control the one or more medical devices, wherein the user input is selected at a graphical user interface displayed on the portable electronic device. The graphical user interface corresponds to a control interface of the one or more medical devices. The method also includes wirelessly controlling the one or more medical devices from the portable electronic device.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION OF THE INVENTION

Figure 1:
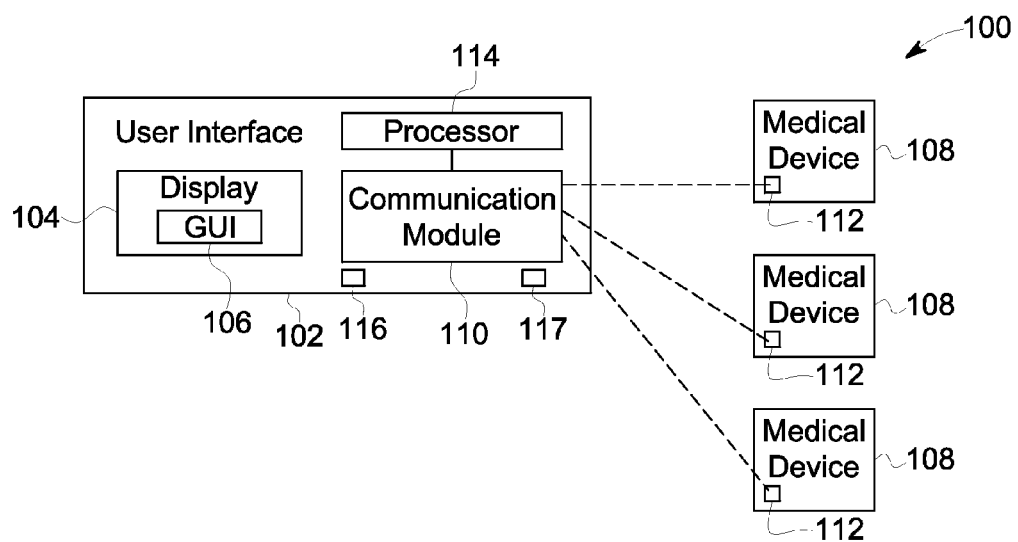
FIG. 1 is a schematic block diagram illustrating a wireless control arrangement in accordance with an embodiment.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein the term "module" refers to software, hardware, for example, a processor, or a combination thereof that is programmed with instructions for carrying an algorithm or method. The modules described herein may communicate wirelessly or through a wired connection.

Various embodiments provide wireless control of medical devices from a user interface, which may be a portable device, such as an electronic tablet type device. However, the user interface may be any portable or handheld device. For example, the tablet type device may be a touch-screen type of computing device. By practicing at least one embodiment, a simpler control interface may be provided that also reduces or eliminates certain points of physical contact between the visiting healthcare practitioner and resident devices. By practicing at least one embodiment, Healthcare-Associated Illnesses (HAIs), in sensitive medical care settings, for example, the Intensive Care Unit (ICU), Operating Room (OR) or Emergency Department (ED) may be reduced.

FIG. 1 is a schematic block diagram illustrating a wireless control arrangement 100 in accordance various embodiments. The wireless control arrangement 100 is illustrated in a medical setting, for example, in an ICU setting. However, the various embodiments may be implemented in different types of healthcare settings or applications. Additionally, the wireless control arrangement 100 may be used in other nonhealthcare settings, such as in environments where physical touching of devices or components should be minimized to the extent possible.

The wireless control arrangement 100 includes a user interface 102, which in one embodiment is a non-dedicated remote device, such as an electronic tablet device or other portable or handheld electronic device. For example, the user interface 102 in one embodiment is a tablet computer device or other mobile computer having a display 104, such as integrated into a flat touch-screen and operable by touching the screen instead of using a physical keyboard. For example, the display 104 may display an onscreen virtual keyboard and also allows use of a passive stylus pen or a digital pen.

It should be noted that the user interface 102 may be embodied in different sizes and shapes, such as based on the particular application and the information to be displayed on the display 104. Thus, the user interface 102 encompasses different form factors and allows different information to be displayed on different portions of the display 104 that may include user selectable elements as described in more detail herein. In some embodiments, an integrated keyboard may be provided that rotates for storage when not in use.

The user interface 102 also provide a graphical user interface (GUI) 106 displayed on the display 104. In one embodiment, the user interface 102 includes pre-loaded applications of different GUIs 106 for communicating with and/or controlling one or more medical devices 108. It should be noted that although three medical devices 108 are illustrated, the user interface 102 may be configured to communicate with additional or fewer medical devices 108. The medical devices 108 may be any type of medical device. In some embodiments, the medical devices 108 are patient care or patient monitoring devices. For example, the medical devices 108 may be monitors, such as blood rate monitors or blood pressure monitors, a ventilator, or an electrocardiogram, among other devices. It should be noted that some of the medical devices 108 may be standalone devices or integrated into a single system.

The user interface also includes a communication module 110 for communicating with the medical devices 108. For example, the medical devices 108 in one embodiment include communication modules 112 that allow bi-directional communication between the user interface 102 and the medical devices 108. The communication modules 110 and 112 may include, for example, a transmitter and received arrangement for communicating therebetween. It should be noted that any suitable wireless communication technology may be used, such as a device to device communication method (e.g., Bluetooth, Infrared control, radio frequency control, etc.), such as to create a personal area network, or a broadcast type of communication method (e.g., WiFi, network, etc.). In various embodiments, the communication scheme or method allows secure communication, such as within a room of a hospital.

The communication module 110 may be configured so as to not interfere with the medical devices 108. The communication module 110 may also communicate using a digital protocol for transmitting information and commands between the user interface 102 and the medical devices 108.

The communication module 110 allow additional functionality, which may be provided in connection with a processor 114 (e.g., central processing unit) and a memory 117. For example, in one embodiment, the communication module 110 includes an application for detecting remote controllable devices (e.g., one or more medical devices 108) in the vicinity of the user interface 102 (e.g., in the ICU ward). The user interface 102 also allows visualization of the medical devices 108, such as by replicating or emulating a control interface of one or more of the medical devices 108 on the display 104 as part of the GUI 106.

Additional components may be provided as part of the user interface 102. For example, a local global positioning system (GPS) device 116 may be provided as part of the user interface 102. The GPS device 116 allows for example, in a medical setting, for the identification of a room location/number, with a log of the medical visit event(s) generated and stored. However, is should be noted that any suitable system or method for locating the user interface 102 may be used and GPS is merely one example. In various embodiments, the memory 117 may store protocol logs, as well as other information, such as time/data sequences downloaded or uploaded to/from the medical devices 108.

It also should be noted that the user interface 102 may be operated in the same location as the medical devices 108, such as in the same room or in a different location than the medical devices, such as outside the room where the medical devices 108 are located, but within the same area (e.g., ICU ward).

In various embodiments, the user interface 102 allows remote control of the medical devices 108 without having to physically touch the medical devices 108. The user interface 102 also allows access to the stored data within the medical devices 108, such as to view or upload monitoring data. The display 104 may display any type of data or images. Thus, the user interface 102 provides real-time control of the medical devices 108.

It should be noted that the user interface 102 may also communicate with other devices using the communication module 110. For example, the user interface 102 may provide communication with peripheral devices, such as printers or scanners. Additionally, the user interface 102 may communicate with a host system, such as a medical data system.

It also should be noted that the user interface 102 may be used for other operations. For example, patient information may be input, such as an observed state of the patient or information received from the patient (e.g., answers to medical questions). Other types of information also may be entered or updated, such as background information, such as patient address and insurance information, as well as, physical information, such as patient height, weight, age, allergies, medical history or the like. Information entered into the user interface 102 or accessed and uploaded from the medical devices 108 may be electronically transmitted to a host system for long term storage.

Other information also may be tracked, such as the time per patient visit, the conditions in the room (e.g., temperature, light level, etc.) or any other information that may be clinically relevant, such as for monitoring the patient and progression of any treatments.

Figure 2:
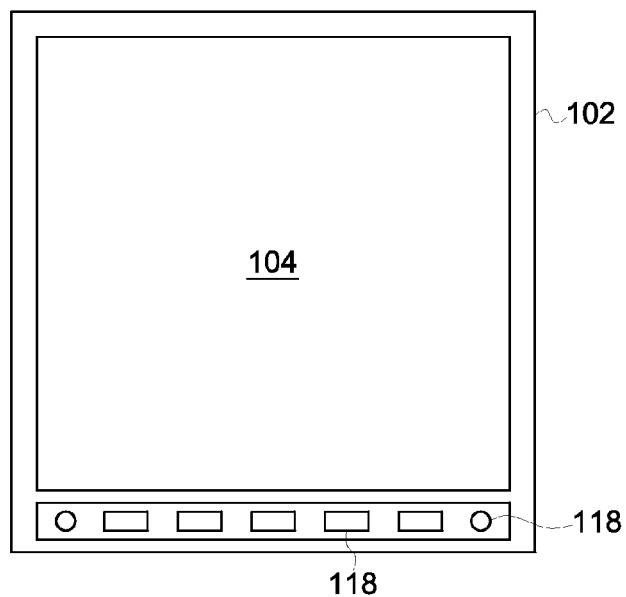
FIG. 2 is a schematic block diagram of a user interface formed in accordance with an embodiment.

FIG. 2 is a simplified schematic block diagram of the user interface 102. FIG. 2 illustrates the user interface 102 as a portable hand-held device. The user interface 102 provides remote control of the medical devices 108 (shown in FIG. 1). For example, the user interface 102 is untethered from the medical devices 108 and may be used remotely therefrom, inside or outside of the room having the medical devices 108. For example, a nurse may directly control the medical devices 108 while observing the patient. Thus, the user interface 102 communicates with the medical devices 108 to control functions and operations of the medical devices 108, which may include, for example, remotely changing settings of the medical devices 108.

The user interface 102 includes the display 104 for displaying information, such as the GUI 106 (shown in FIG. 1). The display 104 includes a resolution capable of displaying desired or required types of information. In one embodiment, the display 104 is a touch sensitive display that also displays information and allows for one or more portions of the display 104 to be touch sensitive portions. For example, at least a portion of the display 104 is able to detect the location of an operator's touch on the display 104. Various types of touch technologies are available for use in touch sensitive displays, including but not limited to touch sensitive elements such as capacitive sensors, membrane switches, and infrared detectors. It also should be noted that the touch sensitive display may be different types of touch sensitive displays. For example, the touch sensitive display may be a single touch display or a multi-touch display. Thus, the display in some embodiments may provide single touch capabilities or multi-touch capabilities (e.g., recognizing two or more points of contact, which may allow scrolling, pinch to zoom, etc, with multiple touches).

The user interface 102 optionally includes one or more input devices 118, such as buttons provided in a keypad that is separate from the display 104. Alternatively, the display 102 may be a touch-screen display having the input devices incorporated therein (e.g. virtual buttons). The user interface 102 may optionally include other components, for example, an audio device, such as a speaker and a microphone.

The user interface 102 may also display as part of the GUI 104 on the display 104 icon-based element or menus for controlling the medical devices 108 as described in more detail below. The icons may have images to facilitate easier identification of associated functions, etc. In some embodiments, the GUI 104 is displayed having an appearance that emulates the appearance of the control interface of one or more of the medical devices 108. It should be noted that the GUI 104 may emulate the display, virtual controls and/or physical controls of the medical device.

Figure 3:
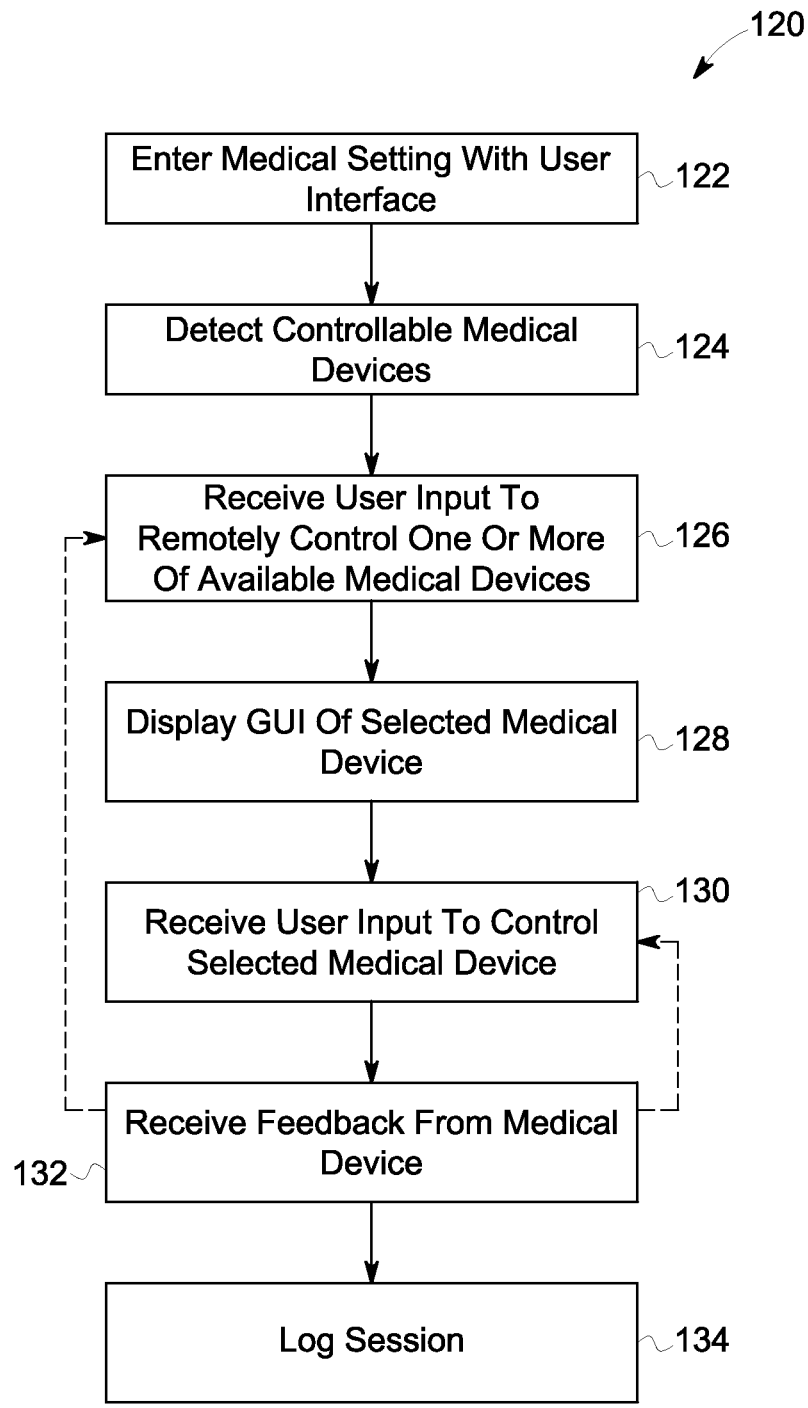
FIG. 3 is a flowchart of a method for wirelessly controlling medical devices in accordance with various embodiments.
Figure 4:
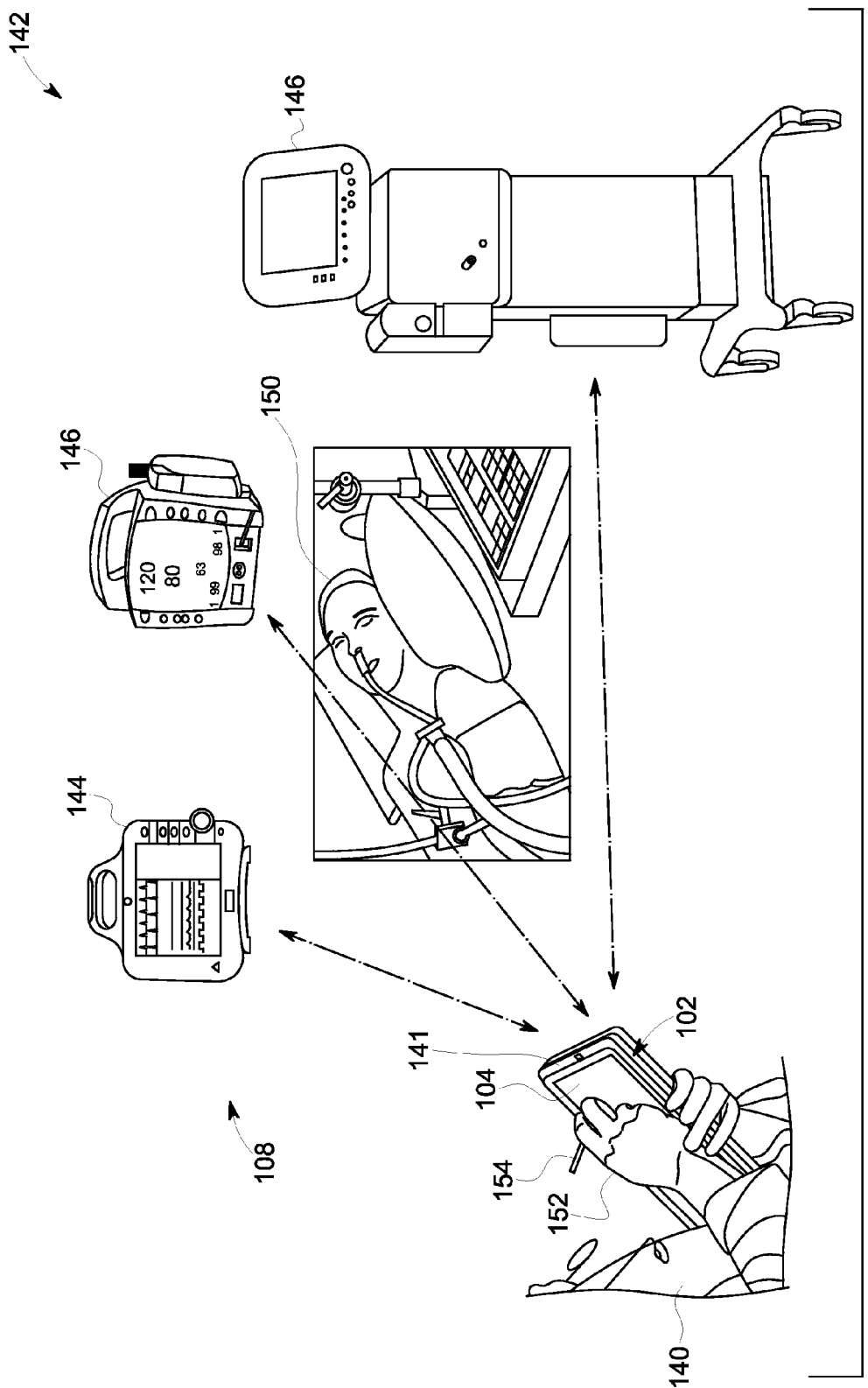
FIG. 4 is a diagram illustrating a wireless control setting in accordance with an embodiment.

FIG. 3 illustrates a method 120 for wirelessly controlling medical devices, such as using or implementing the wireless control arrangement 100. It should be noted that although a particular control/work flow is illustrated, different controls and operations may be provided in the same or different order. In particular, the method 120 in one embodiment includes a clinician entering a medical setting (e.g. ICU ward) at 122 with the user interface 102, for example, carrying a non-dedicated remote control device (e.g. a tablet) to check a patient (e.g., observe a patient that is being monitored). For example, FIG. 4 illustrates a clinician 140 (a portion of the clinician 140 is shown) entering an ICU ward setting 142 to observe a patient 150, as well as to review or control the medical devices 108, which may include remotely obtaining data from or changing one or more settings of one or more of the medical devices 108 with the user interface 102. In this embodiment, the user interface 102 includes a housing 141 having the dimensions of an electronic tablet type device. In the illustrated embodiment, and merely as an example, the medical devices 108 include a heart rate monitor 144, a blood pressure monitor 146 and a ventilator 146 that are coupled to the patient 150 using any suitable technique. As can be seen, the clinician 140 may communicate with and control the medical devices 108 using the user interface 102, such as with the clinician's hand 152, which may include a stylus or other suitable input device.

Figure 5:
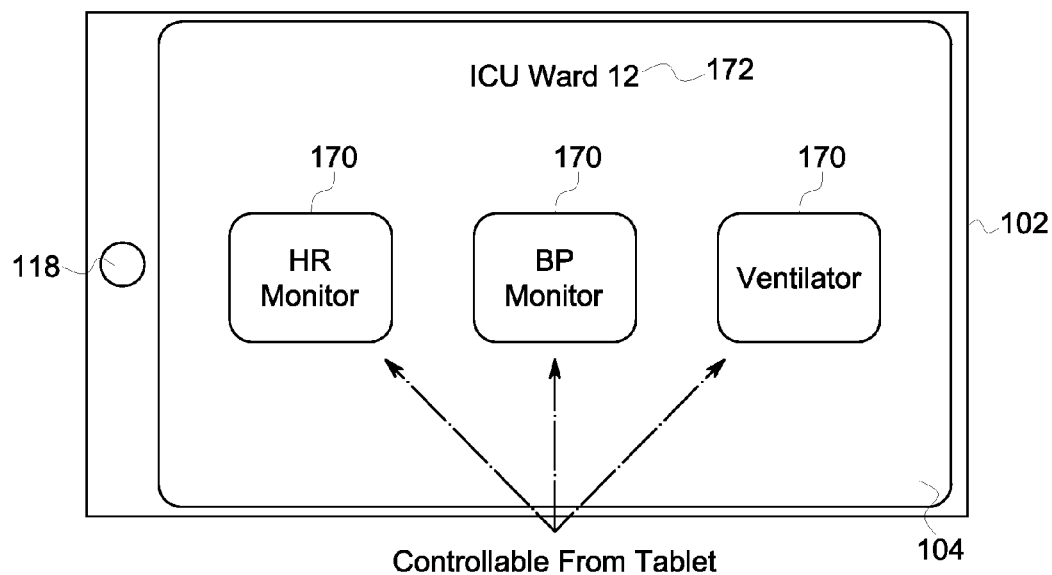
FIG. 5 is a graphical user interface displayed in accordance with an embodiment.

Referring again to FIG. 3, thereafter, controllable medical devices are detected at 124. For example, the user interface 102 may broadcast a query message to the medical devices, such as to the heart rate monitor 144, blood pressure monitor 146 and ventilator 146 (shown in FIG. 4) to determine if any of the devices are remotely controllable with the user interface 102. If one or more of the devices are controllable, a suitable communication handshake technique may be used to establish communication therebetween. In some embodiments, a proximity equipment detection controller may be used to detect available medical devices that may be remotely controlled and acquire information for display on the display 104, for example, as shown in FIG. 5. It should be noted that although the display 104 is shown in a landscape orientation, the user interface 102 may also display information in a portrait orientation with the displayed data appropriately reformatted or reoriented.

In particular, one or more user selectable elements 170 are displayed indicating medical devices that may be remotely controlled. In this example, the selectable elements are icons having text (labels) identifying the medical devices, which may be a generic name or a particular device name. In this embodiment, the user selectable elements 170 correspond to all three of the heart rate monitor 144, blood pressure monitor 146 and ventilator 146, indicating that all of these medical devices are remotely controllable. The display 104 may also provide location information 172 for the devices, such as the particular ward in which the medical devices are located. Thus, the user interface 102 displays on the display 104 the number/type of medical devices in the setting that can be controlled and, for example, the local GPS capability identifies the room number of the medical setting.

Figure 6:
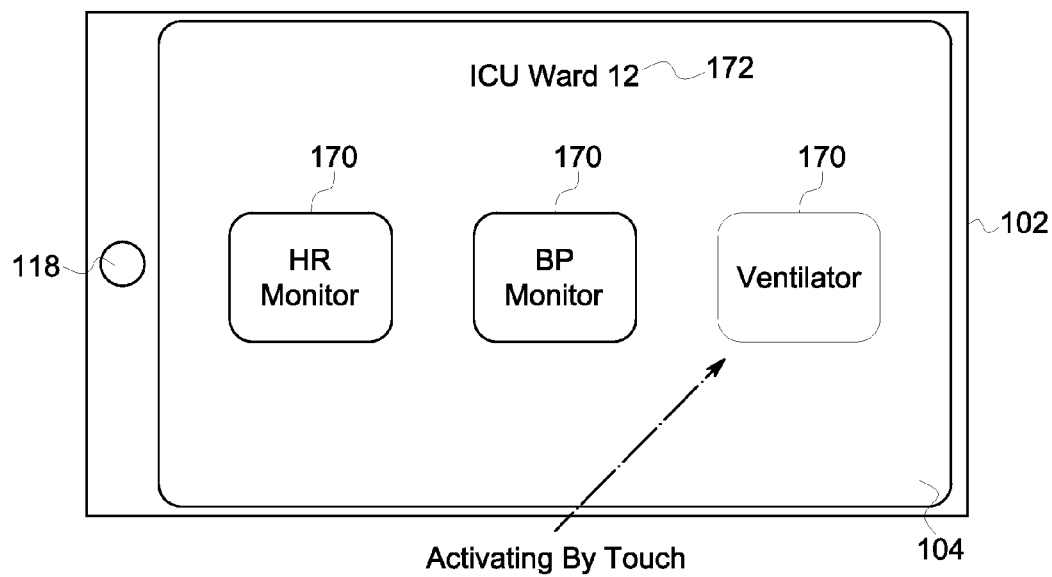
FIG. 6 is a graphical user interface displayed in accordance with another embodiment.

Referring again to FIG. 3, thereafter a user input is received at 126 to remotely control one or more of the identified medical devices. For example, the user may select one of the medical devices with which to establish communication by selecting one of the user selectable elements 170, such as with the user's hand 152 (e.g., a finger of the user) or an input device 154 (e.g., a stylus), which are both shown in FIG. 4. For example, the clinician may activate or initiate remote control of a medical device wherein adjustment needs to be made on the remote control device. FIG. 6 illustrates the clinician 140 activating the user selectable elements 170 corresponding to the ventilator 146. The activation may be indicated, for example, by changing a shading or color of the selected user selectable element 170.

Figure 7:
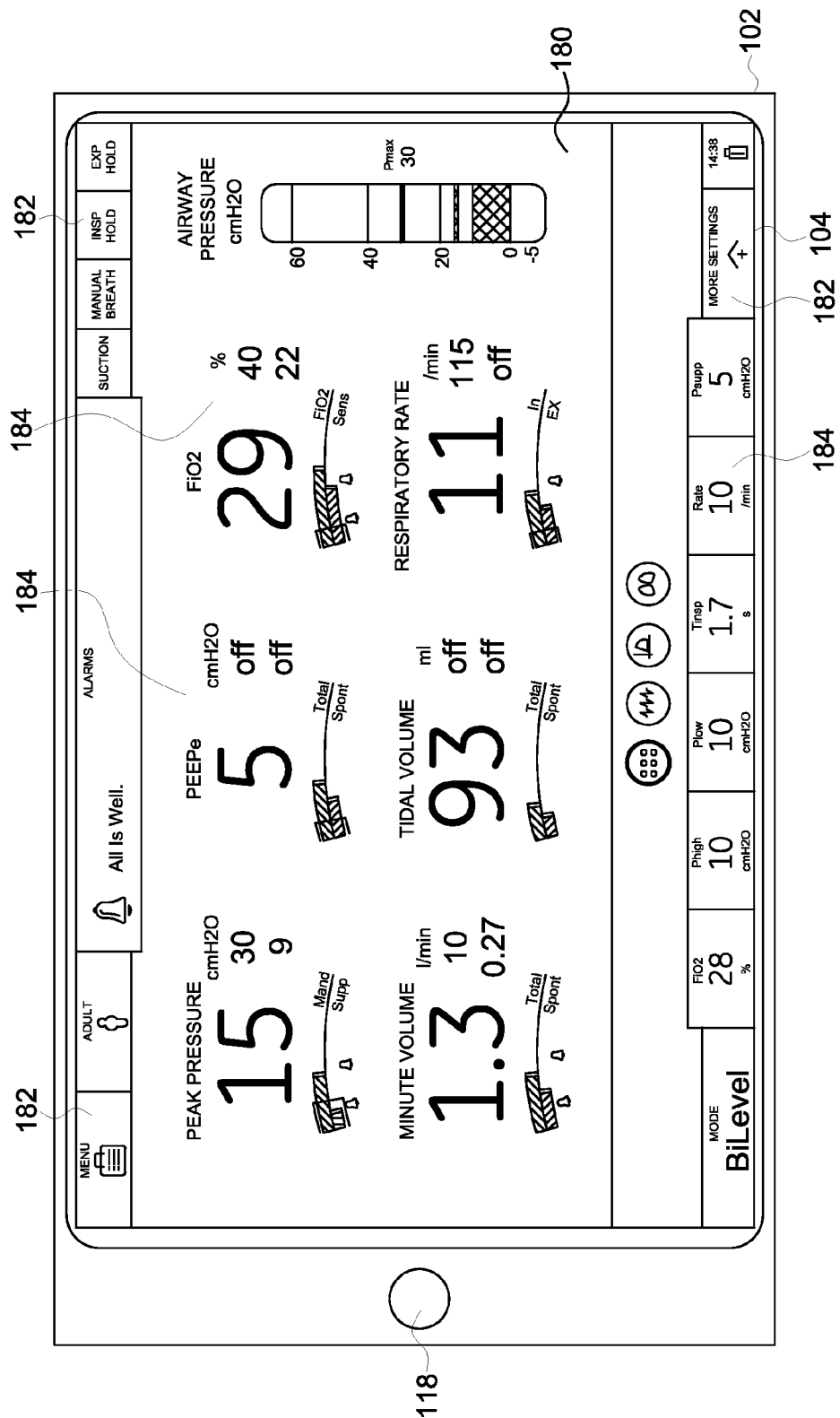
FIG. 7 is a graphical user interface displayed in accordance with another embodiment.

Referring again to FIG. 3, a GUI corresponding to the selected medical device is displayed at 128. In particular, a GUI corresponding to a control interface for the selected medical device is displayed such as shown n FIG. 7, which may be an emulation of the actual GUI on the medical device. For example, the displayed GUI on the user interface 102 may be the same as the displayed GUI on the medical device (or of physical controls of the medical device). In this example, a ventilator GUI 180 is displayed that allows control of the ventilator 146. The controls may provide all or a subset of the control functions available at the medical imaging device, in this case, the ventilator 146. Thus, in this example, the clinician 140 may control the ventilator 146 (e.g., change pressure settings) using the identical control functions and inputs as if physical inputs were provided at the ventilator 146. Accordingly, no physical touching of the medical devices is used in various embodiments.

It should be noted that the user selectable elements and displayed data is merely for illustration and different user selectable elements 182 and data 184 may be displayed. Some of the user selectable elements 182 may activate other GUIs or screens for controlling the ventilator 146. Thus, the clinician 140 may observe current and past readings from the medical device and change settings via the use interface 102, which are transmitted to the medical device. Also, the GUI may be, for example, a software implemented application running on any type of portable computing device.

Accordingly, referring again to FIG. 3, a user input may be received at 130 to control the medical device, such as to change a setting of the medical device. Thereafter, at 130, feedback may be received at 132 from the controlled medical device. For example, the medical device may provide active feedback to the user interface 102 as a result of the change and may show, for example, a potential effect on other control parameters or changes in monitored conditions.

It should be noted that the control of the selected device may be repeated for different settings or to change the same setting to a different value or level such that steps 130 and 132 are repeated. Additionally, a user may select to control another medical device at 126, wherein steps 128-132 are repeated for that medical device, such as displaying the GUI of that device. Accordingly, settings may be adjusted on one or more medical devices in the care setting without physically touching the devices.

The method 120 may also include at 134, upon completion of the visit, generating log of the session. For example, the user interface 102 may generate a log with time stamp and location information (e.g. ICU, ward number, etc.) of the visit and the type of changes/data affected.

Thus, various embodiments provide a wireless system and method for controlling medical devices. The control of the medical devices allows interfacing with the devices without physically touching the devices. At least one technical effect of various embodiments includes minimizing or eliminating touching of medical devices.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A portable user interface for controlling medical devices, the portable user interface comprising:
    a housing;
    a communication module within the housing configured to detect and wirelessly communicate with at least one medical device; and
    a display displaying a plurality of user selectable elements, wherein the communication module is configured to establish bi-directional communication with the at least one medical device based on a selection of at least one of the user selectable elements, and the display displaying a graphical user interface to control the at least one medical device remotely, wherein the displayed graphical user interface corresponds to a control interface of the at least one medical device.

2. The portable user interface of claim 1, wherein the graphical user interface emulates a control interface of the at least one medical device.

3. The portable user interface of claim 1, wherein the communication module detects the at least one medical device based on a proximity of the at least one medical device from the housing.

4. The portable user interface of claim 1, wherein the user selectable elements corresponds to controls for changing settings and operation of the at least one medical device.

5. The portable user interface of claim 1, wherein a number of user selectable elements is based on a number of medical devices detected by the communication module.

6. The portable user interface of claim 1, wherein the display comprises a touch-screen display.

7. The portable user interface of claim 1, further comprising one or more user inputs separate from the display.

8. The portable user interface of claim 1, wherein the housing comprises an electronic tablet type housing.

9. The portable user interface of claim 1, wherein the display displays updated data for the at least one medical device.

10. The portable user interface of claim 1, wherein the displayed graphical user interface displays monitoring data for the at least one medical device.

11. The portable user interface of claim 1, wherein the display displays location information.

12. The portable user interface of claim 1, further comprising a processor for generating a log session corresponding to changes made to settings of the at least one medical device with the graphical user interface.

13. A wireless control arrangement comprising:
    at least one medical device having a communication module; and
    a portable user interface having a housing, a communication module within the housing configured to detect and wirelessly communicate with the at least one medical device, and a display displaying a user selectable element corresponding to the at least one medical device when detected by the communication module, wherein the communication module is configured to establish bi-directional communication with the at least one medical device based on a selection of the user selectable element, and the display displaying a graphical user interface to control the at least one medical device remotely, wherein the displayed graphical user interface corresponds to a control interface of the at least one medical device, and the at least one medical device and the portable user interface communicate via the communication modules.

14. The wireless control arrangement of claim 13, wherein the graphical user interface emulates a control interface of the at least one medical device and wherein the display displays a plurality of user selectable elements for controlling operation of the at least one medical device.

15. The wireless control arrangement of claim 13, further comprising a plurality of medical devices and wherein the display displays a number of user selectable elements corresponding to a number of the plurality of wirelessly controllable medical devices detected by the communication module, and wherein the graphical user interface corresponding to a control interface of a selected one of the medical devices is different than the graphical user interface of another one of the plurality of medical devices.

16. The wireless control arrangement of claim 13, wherein the display comprises a touch-screen display.

17. The wireless control arrangement of claim 13, wherein the at least one medical device comprises a medical monitoring device.

18. A method for controlling a medical device, the method comprising:
    detecting one or more wirelessly controllable medical devices;
    receiving a user input at a portable electronic device to establish communication between the portable electronic device and at least one detected medical device and remotely control the at least one detected medical device, the user input selected at a graphical user interface displayed on the portable electronic device, the graphical user interface corresponding to a control interface of the one or more medical devices; and
    wirelessly controlling the at least one detected medical device from the portable electronic device.

19. The method of claim 18, further comprising emulating the control interface as the graphical user interface.

20. The method of claim 18, further comprising receiving feedback from the at least one detected medical device and displaying the feedback on a display of the portable electronic device.

21. The method of claim 18, further comprising receiving a user input selecting another one of the detected medical devices and displaying a different graphical user interface on the portable electronic device.

22. The method of claim 18, further comprising generating a log session based on the control of the at least one medical device.

* * * * *